US00PP34873P2

(12) United States Plant Patent
van der Sar

(10) Patent No.: US PP34,873 P2
(45) Date of Patent: Dec. 27, 2022

(54) ***PYRACANTHA* PLANT 'ORANGE STAR'**

(50) Latin Name: *Pyracantha coccinea*
Varietal Denomination: Orange Star

(71) Applicant: VOF Van der Sar, 's-Gravenzande (NL)

(72) Inventor: Henk van der Sar, 's-Gravenzande (NL)

( * ) Notice: Subject to any disclaimer, the term of this patent is extended or adjusted under 35 U.S.C. 154(b) by 0 days.

(21) Appl. No.: 17/848,145

(22) Filed: Jun. 23, 2022

(51) Int. Cl.
*A01H 6/74* (2018.01)
*A01H 5/02* (2018.01)

(52) U.S. Cl.
USPC ..... Plt./253

(58) Field of Classification Search
USPC ..... Plt./253
See application file for complete search history.

*Primary Examiner* — Annette H Para
(74) *Attorney, Agent, or Firm* — Cassandra Bright

(57) ABSTRACT

A new and distinct cultivar of *Pyracantha* plant named 'Orange Star' is disclosed, characterized by healthy thornless plants with dark green foliage, and large, bright orange berries. The new variety is a *Pyracantha*, normally produced as an ornamental plant.

3 Drawing Sheets

Latin name of the genus and species: *Pyracantha coccinea.*

Variety denomination: 'ORANGE STAR'.

BACKGROUND OF THE INVENTION

The new *Pyracantha* cultivar is a product of uncontrolled open pollination of unknown *Pyracantha* seedlings. The open pollination resulting in this new variety 'Orange Star' occurred during 2015 at a nursery in 's Gravenzande, the Netherlands.

The new *Pyracantha* variety was discovered in October of 2016 by the inventor in a group of seedlings resulting from the 2015 open pollination, at the same nursery in 's Gravenzande, the Netherlands.

Asexual reproduction of the new cultivar 'Orange Star' by softwood stem cuttings, was first performed during 2017, at the same nursery in 's Gravenzande, the Netherlands. Subsequent propagation by softwood cuttings has shown that the unique features of this cultivar are stable and reproduced true to type in several successive generations.

SUMMARY OF THE INVENTION

The cultivar 'Orange Star' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Orange Star' These characteristics in combination distinguish 'Orange Star' as a new and distinct *Pyracantha* cultivar:

1. Orange berries.
2. Dark green leaves.
3. Not sensitive to fire blight.
4. Large amount of large orange berries from summer into winter.

5. No thorns.
6. Flowers/fruits on 2nd-year-wood.

PARENT COMPARISON

Parent varieties of the new cultivar *Pyracantha* 'Orange Star' cannot be accurately identified for comparison.

COMMERCIAL COMPARISON

Plants of the new cultivar 'Orange Star' can be compared to the variety *Pyracantha* 'Orange Glow', unpatented. These varieties are similar in most horticultural characteristics; however, 'Orange Star' differs in the following:

1. Berries of the new variety are larger than berries of this comparator.
2. Plants of the new variety have no thorns; plants of this comparator do have thorns.
3. Leaves of the new variety are a darker green than leaves of this comparator.
4. The new variety is more resistant to fire blight than this comparator.

Plants of the new cultivar 'Orange Star' can be compared to the variety *Pyracantha* 'Mohave', unpatented. These varieties are similar in most horticultural characteristics; however, 'Orange Star' differs in the following:

1. Berries of the new variety are a lighter orange color; berries of this comparator are more orange-red.
2. Plants of the new variety have no thorns; plants of this comparator do have thorns.
3. The new variety is more resistant to fire blight than this comparator.

BRIEF DESCRIPTION OF THE PHOTOGRAPHS

The accompanying photograph in FIG. 1 illustrates in full color a typical plant of 'Orange Star' shown in a 1-gallon container grown in 's-Gravenzande, the Netherlands.

Figure 1:
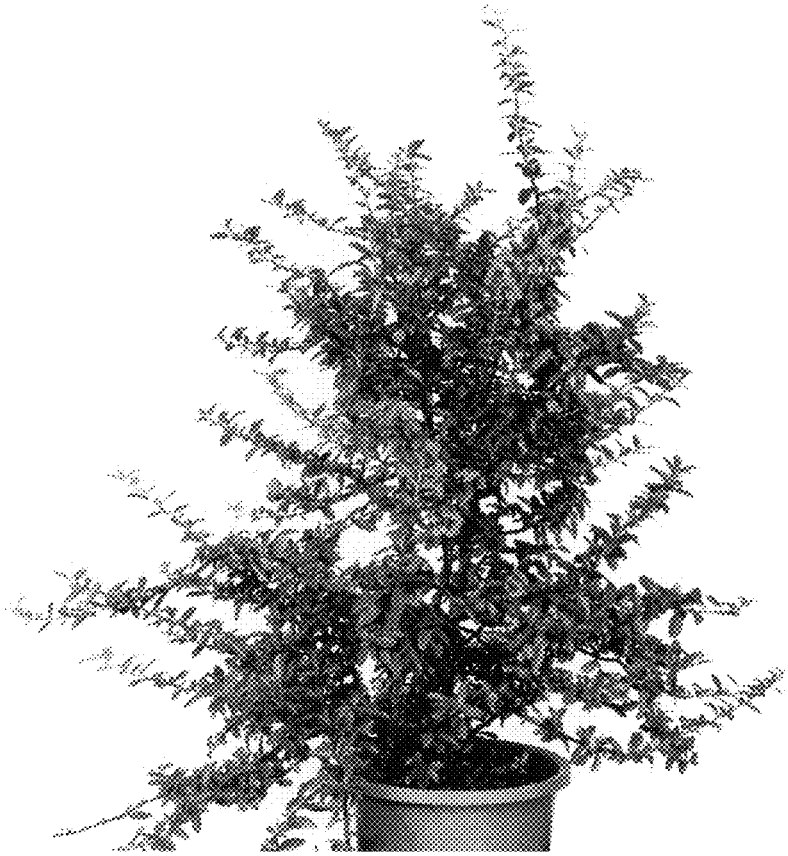
Figure 2:
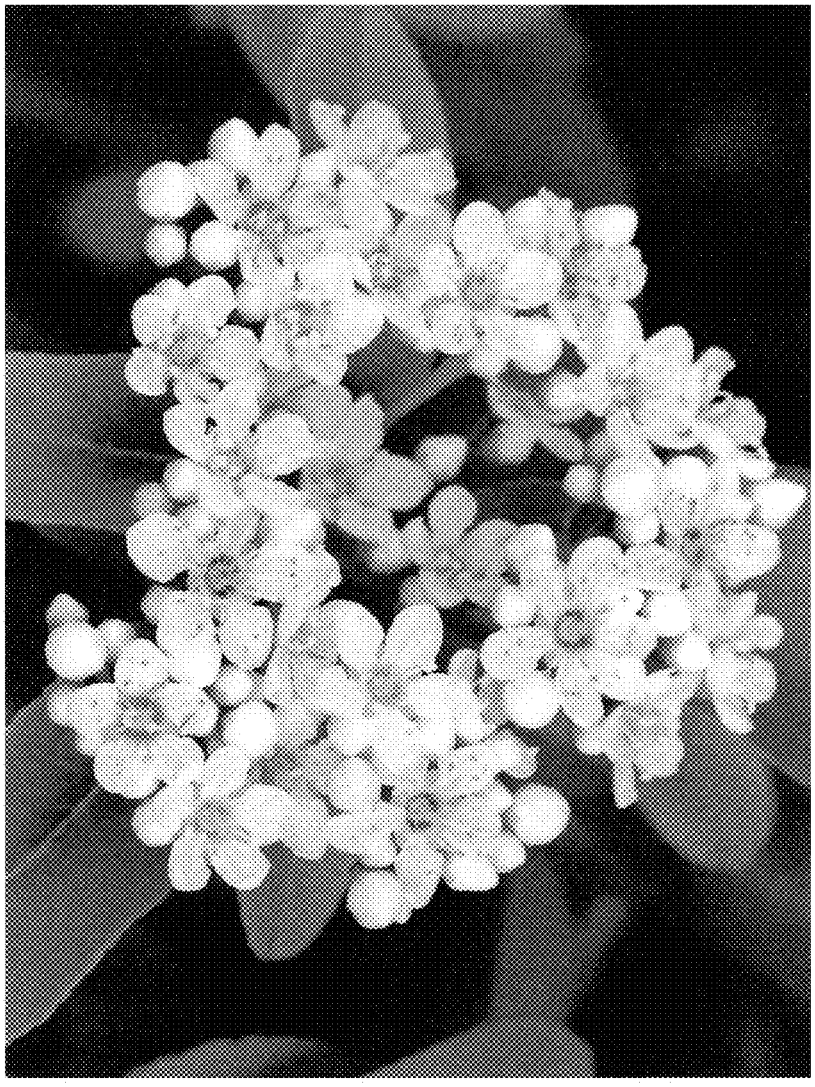
FIG. 2 illustrates in full color flowers of the new variety.
Figure 3:
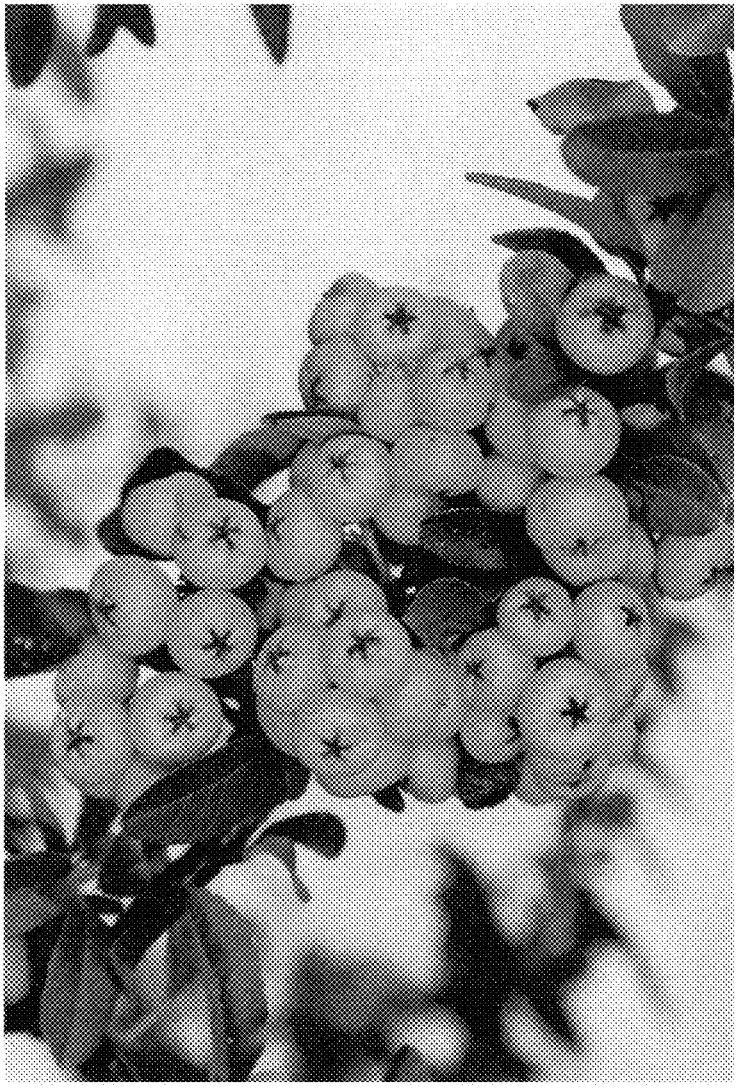
FIG. 3 illustrates a close up of typical fruits of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'Orange Star' plants grown in 's-Gravenzande, the Netherlands, under natural lighting. Measurements were taken during the summer. The plants were 3 years old in 29 cm containers. The growing temperature ranged from 5° C. to 27° C. Measurements and numerical values represent averages of typical plant types.

Botanical classification: *Pyracantha coccinea* 'Orange Star'.

PROPAGATION

Time to initiate roots: About 10 weeks.

Time to produce a rooted young plant: About 8 months.

Roots: Moderate density moderate branching. Medium thickness, fibrous and white in color, not accurately measured with the RHS Chart.

PLANT

Plant type: Perennial evergreen shrub.

Age of plant described: 3 years.

Growth habit: Broad spreading, upright.

Plant shape: Irregular broad ovate.

Height: 106.5 cm to top of foliar plane; 80.5 cm to top of floral plane.

Plant spread: 110 cm.

Growth rate: Moderate to high.

Plant vigor: High.

Branching characteristics: Main stem grows from the base, with lateral branches.

Length of primary lateral branches: 56.5 cm.

Diameter of lateral branches: Average 0.35 cm.

Quantity of lateral branches: 1 per plant.

Quantity of secondary branches: Average 28 per plant.

Internode length: Average 1.2 cm.

Stem:

*Shape.*—Rounded.

*Luster.*—Moderately glossy.

*Angle.*—Average 80°.

*Strength.*—Strong.

*Color.*—Developing: Upper Side: RHS Greyed-Purple 183A. Under Side: RHS Yellow-Green 144A. Mature: Upper Side: RHS Brown N200A. Under Side: RHS Yellow-Green, darker than 152A. At Internodes: Upper Side: RHS Brown N200A. Under Side: RHS Yellow-Green, darker than 152A. Bark. Brown to black: RHS 200A, 200B, N220A, N200B, and 202C.

*Pubescence.*—Moderately to densely covered with a woolly pubescence, colored RHS Greyed-Green 197D.

*Other.*—Occasionally the tip pf a lateral branch grows into a sharp stem spine.

FOLIAGE

Leaf:

*Arrangement.*—Alternate, single.

*Quantity per lateral branch.*—Average 47.

*Leaf shape.*—Elliptic.

*Average length.*—4.3 cm.

*Average width.*—2 cm.

*Apex.*—Acute to bluntly acute.

*Base.*—Short attenuate.

*Margin.*—Finely crenate.

*Texture of top surface.*—Smooth, glabrous, except for main vein, moderately to densely covered with a very short woolly pubescence, colored RHS Greyed-Green 197D.

*Texture of bottom surface.*—Smooth, glabrous.

*Rugosity.*—Both sides non-rugose.

*Luster.*—Upper Side: Slightly to moderately glossy. Under Side: Matte.

*Lobed.*—Unlobed.

*Color.*—Young foliage upper side: Near RHS Green 137A. Young foliage under side: Near RHS Green 138B. Mature foliage upper side: RHS Green NN137A to Yellow-Green 147A. Mature foliage under side: RHS Yellow-Green to Greyed-Green, blend of 147B and 191B.

*Venation.*—Pattern: Pinnate. Color upper side: RHS Yellow-Green 146B to 146C. Color under side: RHS Yellow-Green 146D.

*Petiole.*—Average Length: 0.8 cm. Diameter: 0.125 cm. Color upper side: RHS Yellow-Green 144A. Color lower side: RHS Yellow-Green 144B. Texture upper side: Moderately covered with a very short woolly pubescence, colored greyed-green; 197D. Texture lower side: Smooth, Glabrous. Luster: Upper Side: Very slightly glossy. Under Side: Slightly glossy.

*Strength.*—High.

FLOWER

Natural flowering season: Spring.

Flower arrangement: Compound corymb, axillary and terminal.

Inflorescence type and habit: Compound corymb.

Inflorescence height: 3.9 cm.

Inflorescence width: 5.1 cm.

Quantity of flowers per inflorescence: Average 100.

Quantity of flowers per plant: Average 1500.

Individual flowers:

*Flower form.*—Single, rotate.

*Flower shape.*—Rotate.

*Flower aspect.*—Upright.

*Size.*—Diameter: 1.2 cm. Length: 1.2 cm. Depth: 0.5 cm.

Flower other characteristics:

*Persistence.*—Self-cleaning.

*Fragrance.*—Faint, typical Pyracanths-scent, slightly unpleasant.

Petal:
*Arrangement.*—Rotate.
*Number of petals per flower.*—5.
*Petal fused.*—No, base implanted in cup-shaped lower 62.5% of calyx.
*Petal shape.*—Broad ovate, slightly concave.
*Petal base.*—Cuneate.
*Margin.*—Entire.
*Tip shape.*—Bluntly acute.
*Length.*—0.5 cm.
*Width.*—0.3 cm.
*Texture.*—Smooth, glabrous, both sides.
*Rugosity.*—Non-rugose, both sides.
*Luster.*—Matte, both sides.
*Color.*—When opening: Upper surface: RHS White 155C. Lower surface: RHS White 155C. Fully opened: Upper surface: RHS White NN155B to NN155C. Lower surface: RHS White NN155B. Fading: Upper surface: RHS White 155C to 155D. Lower surface: RHS White 155C.

Bud:
*Shape.*—Broad elliptic.
*Length.*—0.45 cm.
*Diameter.*—0.3 cm.
*Color.*—Upper half: RHS Green-White 157D. Lower half: RHS Yellow-Green 144B.
*Texture.*—Smooth, glabrous.
*Luster.*—Matte.

Calyx:
*Shape.*—Rotate.
*Length.*—0.25 cm.
*Diameter.*—0.5 cm.

Sepals:
*Arrangement.*—Rotate, lower 62.5% fused.
*Number.*—5.
*Shape.*—Free part triangular, lower 62.5% fused.
*Base.*—Broad cuneate.
*Margin.*—Entire.
*Tip shape.*—Acute.
*Length.*—0.4 cm.
*Width.*—At base of free part: 0.15 cm.
*Color.*—When opening, upper side: RHS Yellow-Green 145C. When opening, under side: Free part RHS Yellow-Green 145B, fading lighter towards the margins; 145C to 145D, fused lower 62.5% darker; 144B. Fully opened, upper side: RHS Yellow-Green 145B. Fully opened, under side: Free part RHS Yellow-Green 145A, fading lighter towards the margins; 145B to 145C, fused lower 62.5% darker; 144B.
*Texture, upper side.*—Smooth, glabrous.
*Texture, lower side.*—Smooth, glabrous.
*Luster, upper side.*—Matte.
*Luster, lower side.*—Matte.

Peduncle:
*Length.*—2.4 cm.
*Diameter.*—0.1 cm.
*Color.*—RHS Yellow-Green 144B.
*Strength.*—Strong.
*Texture.*—Sparsely covered with a very thin pubescence, average length of hairs: 0.1 cm, colored white; impossible to measure with RHS-CC due to sparseness and small size.
*Angle.*—Average 25°.
*Luster.*—Slightly glossy.

Pedicels:
*Length.*—0.25 cm.
*Diameter.*—0.075 cm.
*Angle.*—Average 20°.
*Strength.*—Medium-strong.
*Texture.*—Sparsely covered with a very thin pubescence, average length of hairs: 0.1 cm, colored white; impossible to measure with RHS-CC due to sparseness and small size.
*Luster.*—Slightly glossy.
*Color.*—RHS Yellow-Green 144B.

REPRODUCTIVE ORGANS

Stamens:
*Number.*—Average 20.
*Filament length.*—0.3 cm, base implanted in cup-shaped lower 62.5% of calyx.
*Filament color.*—RHS White 155C.

Anthers:
*Shape.*—Broad oblong.
*Length.*—0.5 cm.
*Width.*—0.5 cm.
*Color.*—RHS White 155A.
*Pollen color.*—White, too low amount to be measured with RHS-CC.
*Pollen amount.*—Low.

Pistil:
*Number.*—1, occasionally 2.
*Lngth.*—0.3 cm.
*Style.*—Length: 0.2 cm. Color: RHS Yellow-Green 145A.
*Stigma.*—Shape: Split in an average of 3 stigmas, occasionally 2, 4 or 5. Color: RHS Yellow-Green 145B. Ovary Color: RHS Yellow-Green 147B; top of ovary densely covered with a short pubescence; average length of hairs 0.1 cm; colored RHS White N155A.

OTHER CHARACTERISTICS

Fruit:
*Quantity.*—Approximately 750 per plant.
*Length.*—0.9 cm.
*Width.*—1.2 cm.
*Texture.*—Smooth, glabrous, very slightly to slightly glossy.
*Color.*—RHS Orange-Red N30C, fading lighter at the base to 30B.

Seeds:
*Quantity.*—Average 5 per fruit.
*Length.*—0.3 cm.
*Diameter.*—0.3 cm.
*Texture.*—Smooth, glabrous.
*Color.*—RHS Brown 200D.

Disease/pest resistance: Observed not sensitive for fire blight. Otherwise typical of the species.

Temperature tolerance: Tolerance range between −15° C. to 35° C.

What is claimed is:

1. A new and distinct cultivar of *Pyracantha* plant named 'Orange Star' as herein illustrated and described.

* * * * *